(12) United States Patent
Byeon et al.

(10) Patent No.: US 6,258,028 B1
(45) Date of Patent: Jul. 10, 2001

(54) PORTABLE ULTRASONIC DIAGNOSTIC APPARATUS FOR VETERINARY ACTIVITY

(75) Inventors: Jong-Won Byeon; Woo-Jung Lee; Sang-Jae Lee, all of Seoul (KR)

(73) Assignee: Medison Co., Ltd. (KR)

( * ) Notice: Subject to any disclaimer, the term of this patent is extended or adjusted under 35 U.S.C. 154(b) by 0 days.

(21) Appl. No.: 09/393,111

(22) Filed: Sep. 10, 1999

(30) Foreign Application Priority Data

Feb. 12, 1999 (KR) .................................................... 99-5017

(51) Int. Cl.⁷ ........................................................ A61B 8/00
(52) U.S. Cl. .............................................. 600/437; 600/459
(58) Field of Search .................................... 600/388, 588, 600/390, 431, 436, 437, 446, 459; 73/625–626; 367/7

(56) References Cited

U.S. PATENT DOCUMENTS

| | | |
|---|---|---|
| 3,017,567 | 1/1962 | Barringer et al. . |
| 4,226,229 | 10/1980 | Eckhart et al. . |
| 4,561,576 | 12/1985 | Lowe et al. . |
| 4,920,969 * | 5/1990 | Suzuki et al. .......................... 600/436 |
| 5,007,427 * | 4/1991 | Suzuki et al. .......................... 600/436 |
| 5,111,818 * | 5/1992 | Suzuki et al. .......................... 600/388 |
| 5,438,996 | 8/1995 | Kemper et al. . |
| 5,853,005 * | 12/1998 | Scanlon ................................ 600/459 |
| 5,913,834 * | 6/1999 | Francais ............................... 600/591 |
| 6,126,608 * | 10/2000 | Kemme et al. ....................... 600/459 |

* cited by examiner

Primary Examiner—Francis J. Jaworski
Assistant Examiner—Ali M. Imam
(74) Attorney, Agent, or Firm—F. Chau & Associates, LLP (57) ABSTRACT

A portable ultrasonic diagnostic apparatus is provided. The portable ultrasonic diagnostic apparatus can be worn and carried on the shoulder, so that an activity for diagnosing a health condition of animals on the farm or open field can be put more simply and swiftly into practice. The portable ultrasonic diagnostic apparatus includes an ultrasonic diagnoser and a shoulder-wear member combined with the ultrasonic diagnoser so that the ultrasonic diagnoser can be put on the shoulder.

15 Claims, 8 Drawing Sheets

PORTABLE ULTRASONIC DIAGNOSTIC APPARATUS FOR VETERINARY ACTIVITY

BACKGROUND OF THE INVENTION

1. Field of the Invention

The present invention relates to a portable ultrasonic diagnostic apparatus having a probe for veterinary activity which is referred to as an ultrasonic diagnostic apparatus, and more particularly, to an ultrasonic diagnostic apparatus which is worn on his or her shoulder in order to diagnose a health condition of an animal on the farm or field.

2. Description of the Related Art

In general, an ultrasonic diagnostic apparatus is hand-held or hand-carrying diagnostic equipment for diagnosing a health condition of animals using an ultrasonic signal.

Figure 1:
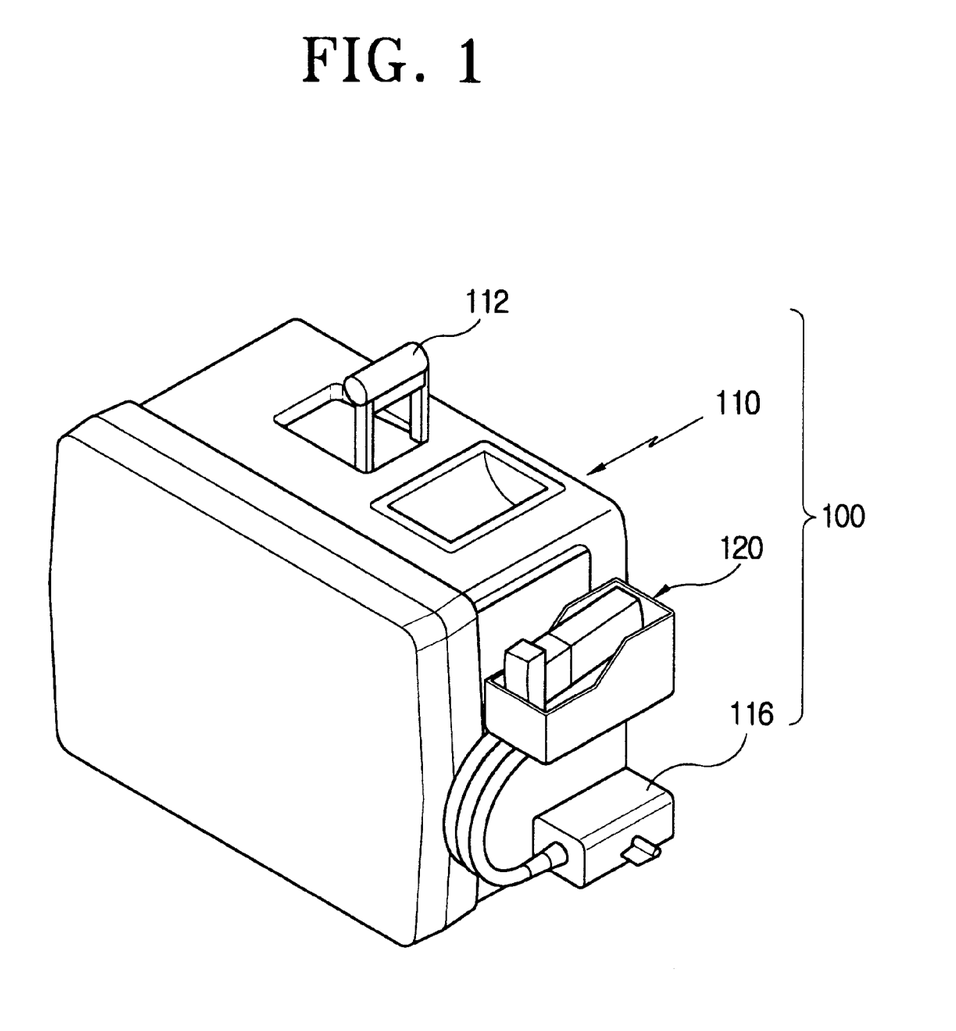
FIG. 1 is a perspective view showing a conventional ultrasonic diagnostic apparatus.

One of conventional ultrasonic diagnostic apparatuses is shown in FIG. 1, which will be described below in detail.

A conventional ultrasonic diagnostic apparatus 100 is shown in FIG. 1. The ultrasonic diagnostic apparatus 100 includes an ultrasonic diagnoser 110 incorporated with a system for generating an ultrasonic wave and processing the generated ultrasonic wave. A grip 112 is provided on the upper surface of the ultrasonic diagnoser 110, and a terminal plate 116 is provided on the lateral surface thereof. A probe 120 for transmitting an ultrasonic signal transmitted from the ultrasonic diagnoser 110 to an external target object and then receiving an ultrasonic signal reflected and returned from the object, is connected with the terminal plate 116.

In the above conventional ultrasonic diagnostic apparatus 100, the grip 112 enables a user to hold the ultrasonic diagnoser 110 by hand and to hand-carry it.

However, the ultrasonic diagnostic apparatus 100 is heavy in its weight due to the components incorporated in the ultrasonic diagnoser 110 and large in its volume. Thus, it is inconvenient for a user to hand-hold it for a long time or to use it in the hand-carried state. In particular, it is difficult to perform a mobile diagnostic activity in correspondence to movement of animals on the farm or field.

SUMMARY OF THE INVENTION

To solve the above problems, it is an object of the present invention to provide an ultrasonic diagnostic apparatus which is portable and wearable.

It is another object of the present invention to provide an ultrasonic diagnostic apparatus which is portable and wearable, in which an ultrasonic diagnoser is accommodated quickly and simply.

It is still another object of the present invention to provide an ultrasonic diagnostic apparatus which is improved a safety in carrying it, with which an ultrasonic diagnoser is firmly combined.

To accomplish the object according to one aspect of the present invention, there is provided an ultrasonic diagnostic apparatus comprising: an ultrasonic diagnoser; and a shoulder-wear member which is combined with the ultrasonic diagnoser in order to enable the ultrasonic diagnoser to be worn on the shoulder.

The ultrasonic diagnostic apparatus comprises a battery case which is assembled or disassembled to one surface of the ultrasonic diagnoser.

The ultrasonic diagnostic apparatus comprises a back supporting member located between the ultrasonic diagnoser and the shoulder-wear member and made of a grid-shaped plate material combined with the ultrasonic diagnoser, in order to mitigate a sense of oppression loaded from the ultrasonic diagnoser to the human body.

The ultrasonic diagnostic apparatus comprises a waist band member connected to the back supporting member in which a belt and a pair of buckles in either end of the belt are formed.

The ultrasonic diagnostic apparatus comprises an external monitor connected to the ultrasonic diagnoser in order to output a detected signal as an ultrasonic image.

To accomplish another object according to another aspect of the present invention, there is also provided an ultrasonic diagnostic apparatus comprising: an ultrasonic diagnoser; a box-shaped back supporting member having a space for accommodating the ultrasonic diagnoser; and a shoulder-wear member which is connected to the back supporting member in order to enable the ultrasonic diagnoser to be worn on the shoulder.

The ultrasonic diagnostic apparatus comprises a battery case which is assembled or disassembled to one surface of the back supporting member, in order to accommodate outer sheathed batteries.

The ultrasonic diagnostic apparatus comprises a waist band member connected to the back supporting member in which a belt and a pair of buckles in each end of the belt are formed.

The ultrasonic diagnostic apparatus comprises an external monitor connected to the ultrasonic diagnoser in order to output a detected signal as an ultrasonic image.

To accomplish the other object according to another aspect of the present invention, there is also provided an ultrasonic diagnostic apparatus comprising: an ultrasonic diagnoser having an engagement portion pierced with a throughhole and formed in each corner portion; a battery case including an opening and shutting cover hinge-combined and a supporting leg pierced with a throughhole corresponding to the engagement portion of the ultrasonic diagnoser in each corner portion, and being combined with one surface of the ultrasonic diagnoser; a back supporting member having a supporting leg pierced with a throughhole corresponding to the engagement portion of the ultrasonic diagnoser in each corner portion and combined with the other surface of the ultrasonic diagnoser; and a shoulder-wear member which is connected to the back supporting member in order to enable the ultrasonic diagnoser to be worn on the shoulder.

In the ultrasonic diagnostic apparatus, both surfaces of the engagement portion of the ultrasonic diagnoser are concave by a predetermined depth, and the supporting legs of back supporting member and the battery case are bent in correspondence to the engagement portion.

The ultrasonic diagnostic apparatus comprises a waist band member connected to the back supporting member in which a belt and a pair of buckles in each end of the belt are formed.

The ultrasonic diagnostic apparatus comprises an external monitor connected to the ultrasonic diagnoser in order to output a detected signal as an ultrasonic image.

BRIEF DESCRIPTION OF THE DRAWINGS

The objects and other advantages of the present invention will become more apparent by describing in detail the structures and operations of the present invention with reference to the accompanying drawing, in which.

DETAILED DESCRIPTION OF THE PREFERRED EMBODIMENTS

Preferred embodiments of the present invention will be described with reference to the accompanying drawings.

Figure 2:
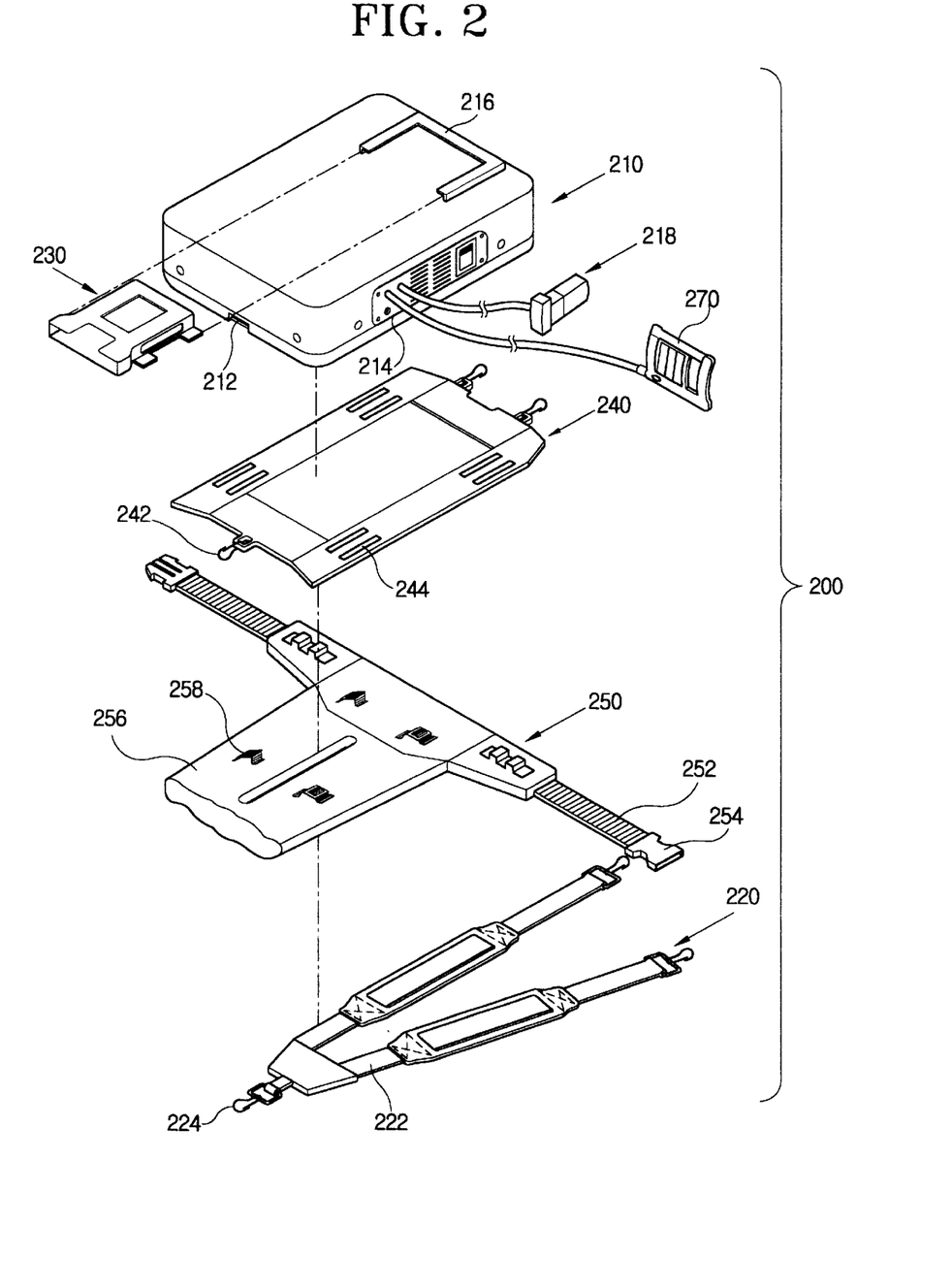
FIG. 2 is a perspective view of a disassembled state of a first preferred embodiment of the present invention.
Figure 3A:
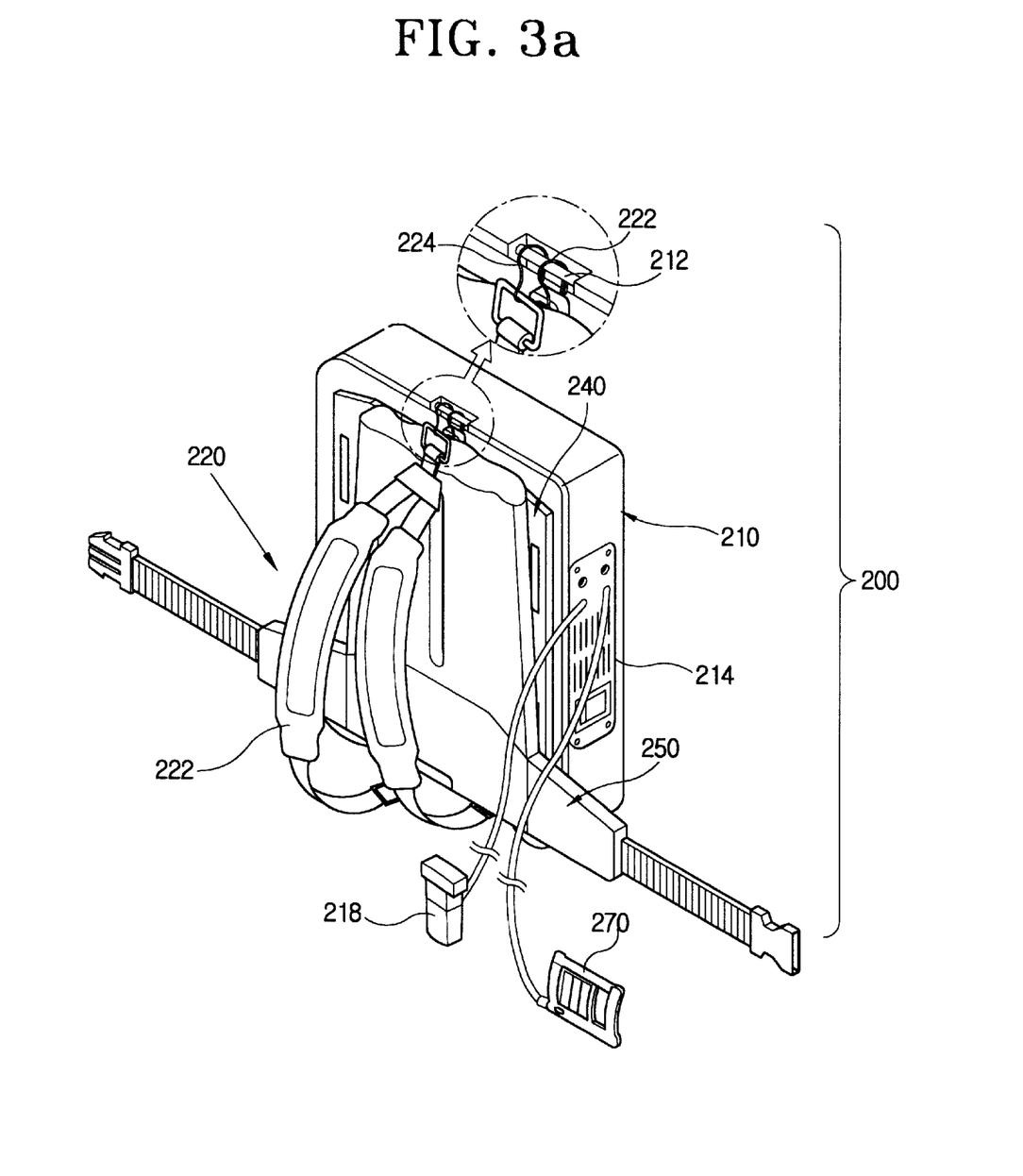
FIG. 3a is a perspective view showing a front side of the assembled state of the first embodiment.
Figure 3B:
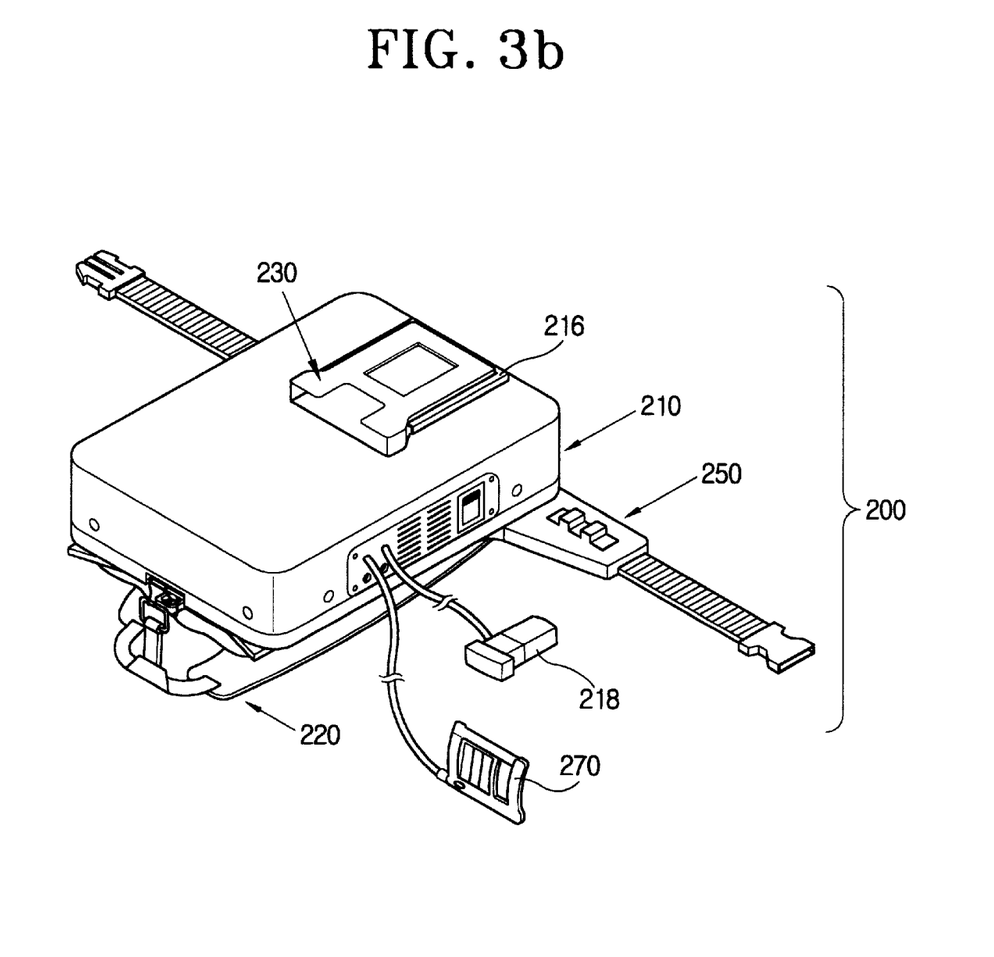
FIG. 3b is a perspective view showing a rear side of the assembled state of the first embodiment.

FIG. 2 shows a disassembled state of an ultrasonic diagnostic apparatus 200 of a first preferred embodiment of the present invention. FIG. 3a is a perspective view showing a front side of the assembled state of the first embodiment. FIG. 3b is a perspective view showing a rear side of the assembled state of the first embodiment.

The ultrasonic diagnostic apparatus 200 includes an ultrasonic diagnoser 210, a shoulder-wear member 220, a battery case 230, a back supporting member 240 and a waist band member 250.

The ultrasonic diagnoser 210 has a system for generating an ultrasonic signal and processing it incorporated therein, in which the shape of the ultrasonic diagnoser is a substantially flat hexahedron.

Ring connection portions 212 are formed on the upper and lower edges of the front surface of the ultrasonic diagnoser 210. The ring connection portions 212 are formed as one on the upper edge and two on the lower edge. A terminal plate 214 is formed in the lateral surface of the ultrasonic diagnoser 210, and a battery case holder 216 for mounting a battery case in the rear end. A probe 218 and an external monitor 270 are connected on the terminal plate 214.

The shoulder-wear member 220 is comprised of a substantially V-shaped shoulder strap 222 and rings 224 formed on respective ends of the shoulder strap 222.

The battery case 230 is formed as a substantially flat hexahedron shape corresponding to an outer sheathed battery.

The back supporting member 240 is formed as a grid-shaped plate material corresponding to the shape of the ultrasonic diagnoser 210. On the upper and lower edges of the back supporting member 240 are formed the rings 242 in correspondence to each ring connection portion 212 of the ultrasonic diagnoser 210, and in its lateral surface are formed four band combining portions 244.

The waist band member 250 is comprised of a belt 252, a pair of buckles 254 mutually corresponding to either end of the belt 252, and a buffer member 256 corresponding to the back supporting member 240. On the rear surface of the waist band member 250 are formed four combining bands 258 corresponding to the band combining portion 244 of the back supporting member 240.

The battery case 230 is inserted into the battery case holder 216 formed on the rear surface of the ultrasonic diagnoser 210. The combining bands 258 of the waist band member 250 are combined with the band combining portions 244 of the back supporting member 240. The rings of the back supporting member 240 are connected with the ring connection portions 212 of the ultrasonic diagnoser 210. The shoulder-wear member 220 is combined with the ultrasonic diagnoser 210 through the rings 224 connected to the ring connection portions 212 in front of the back supporting member 240. The state of the completely combined ultrasonic diagnostic apparatus 200 is shown in FIGS. 3a and 3b.

In the ultrasonic diagnostic apparatus 200 according to the present invention, the battery case 230 is made in such a manner that its separation and assembly work is simply and quickly done in order to charge a battery or replace a battery by another. The back supporting member 240 helps the ultrasonic diagnoser 210 supported more safely at the back of a human body. Also, the back supporting member 240 helps other members relating to the waist band member 250 and so on simply combined with the ultrasonic diagnoser 210, by mediating the links. The waist band member 250 makes the ultrasonic diagnoser 210 fixed to the waist and prevents the former from being swayed in use, thereby improving a safety when carrying it. The buffer member 256 protects the human body from a mechanical shock transmitted from the ultrasonic diagnoser 210, thereby rendering a comfortable wearing. The external monitor 270 allows a user to identify a diagnosis result at once as an ultrasonic image during diagnosing the health condition.

The shoulder-wear member 220 allows a user to carry the ultrasonic diagnoser 210 on the shoulder conveniently. If the ultrasonic diagnoser 210 is used after being carried on the shoulder, inconveniences and consumption of the physical strength are greatly reduced compared with the case when the ultrasonic diagnoser 210 is used while being gripped by hand. Thus, the user can use the ultrasonic diagnoser 210 for a longer time. In addition, since the ultrasonic diagnoser 210 can be carried more conveniently, an activity for diagnosing a health condition can be done more swiftly in correspondence to the movement of the animals in the open field such as an animal farm. Further, the ultrasonic diagnostic apparatus 200 according to the present invention enables a user to connect other related devices to the ultrasonic diagnoser 210 as necessary indoors such as a laboratory.

Figure 4:
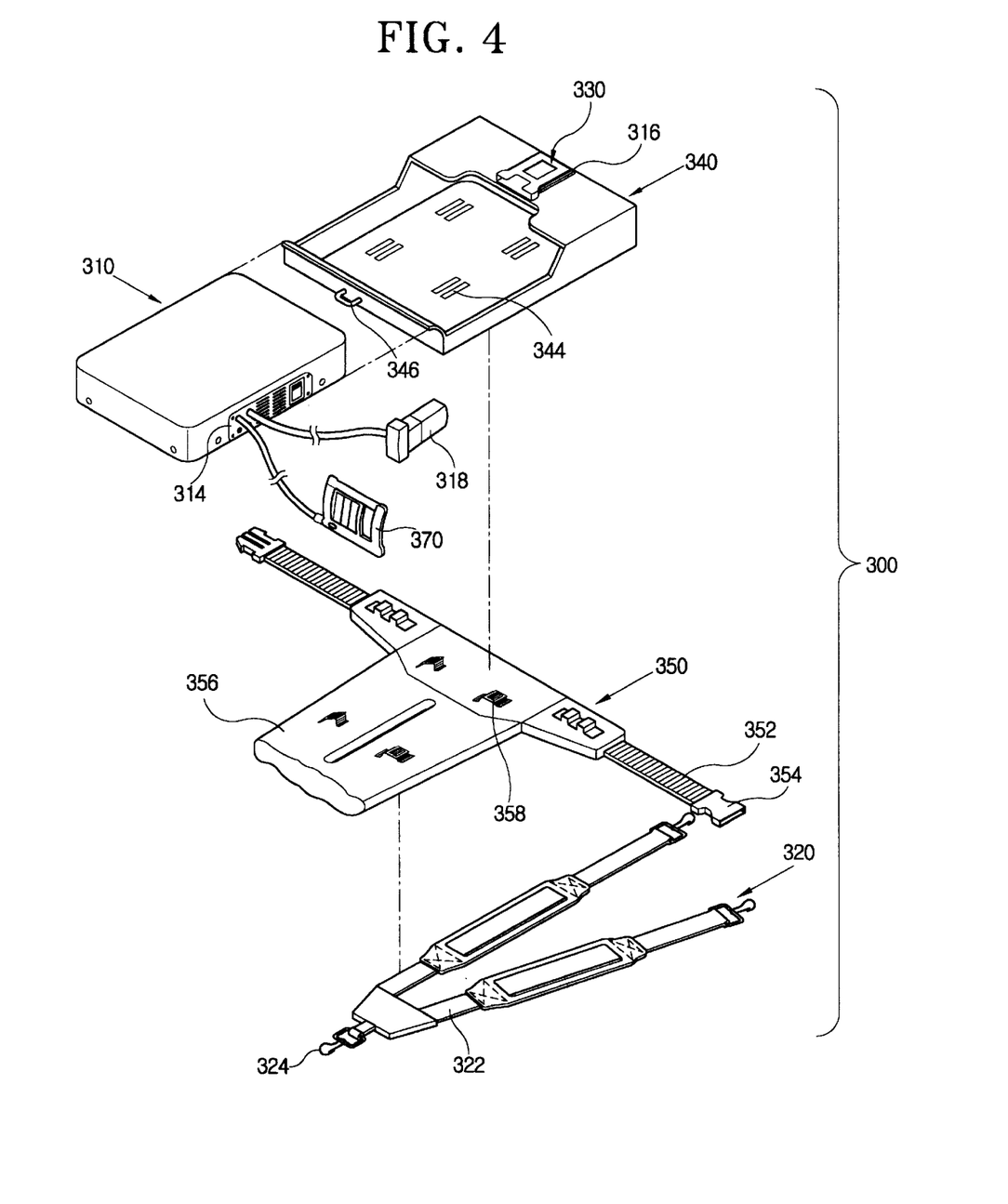
FIG. 4 is a perspective view of a disassembled state of a second preferred embodiment of the present invention.
Figure 5:
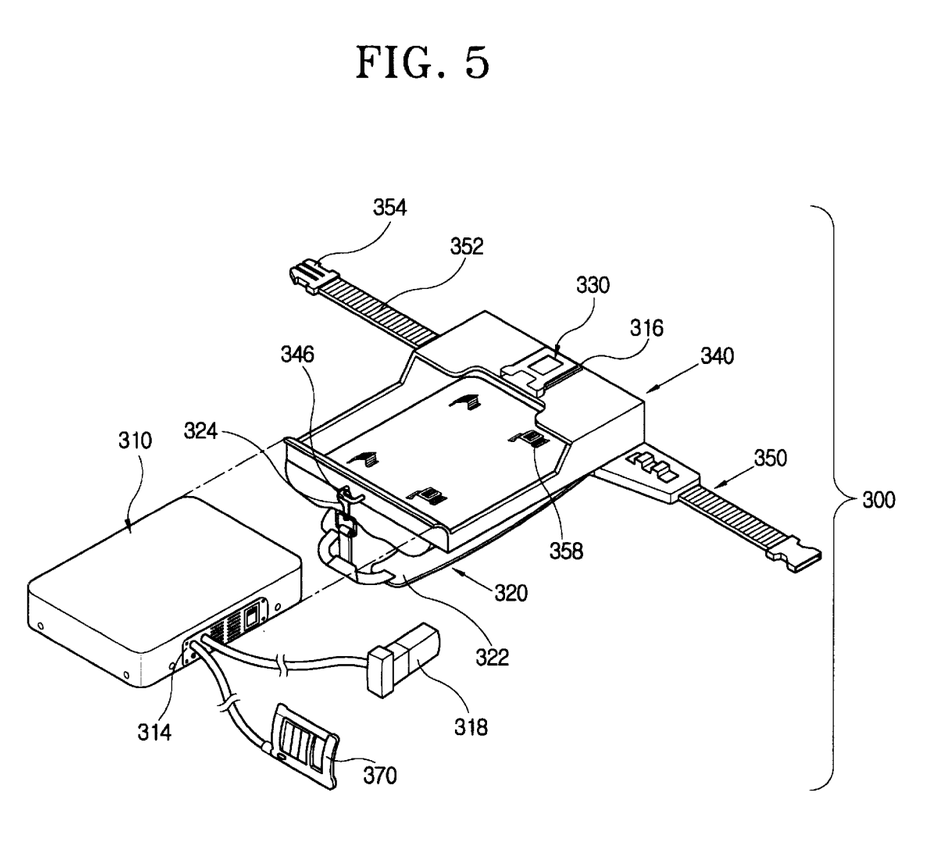
FIG. 5 is a perspective view of an assembled state of the second embodiment'

FIG. 4 is a perspective view of a disassembled state of a second preferred embodiment of the present invention. FIG. 5 is a perspective view of an assembled state of the second embodiment.

An ultrasonic diagnostic apparatus 300 of the second embodiment is shown in FIG. 4. The ultrasonic diagnostic apparatus 300 is comprised of an ultrasonic diagnoser 310, a shoulder-wear member 320, a battery case 330, a back supporting member 340 and a waist band member 350. The ultrasonic diagnoser 310 has a system for generating an ultrasonic signal and processing it incorporated therein, in which the shape of the ultrasonic diagnoser is a substantially flat hexahedron. A terminal plate 314 is formed in the lateral surface of the ultrasonic diagnoser 310, and a probe 318 and an external monitor 370 are connected on the terminal plate 314. The shoulder-wear member 320 is comprised of a shoulder strap 322 and rings 324 formed on respective ends of the shoulder strap 322. The battery case 330 is formed as a substantially flat hexahedron whose one side is open. The back supporting member 340 is formed as a substantially box shape having a space for accommodating the ultrasonic diagnoser 310. One side of the back supporting member 340 is open in part so that the space communicates with the outside. Three ring connection portions 346 are formed in the upper and lower edges of the back supporting member 340, four band combining portions 344 are formed in the front surface thereof, and a battery case holder 316 for inserting the battery case 330 is formed in the rear surface thereof. The waist band member 350 is comprised of a belt 352, a pair of buckles 354 mutually corresponding to either end of the belt 352. At the center of the waist band member 350 is formed a buffer member 356 corresponding to the back supporting member 340.

Rings 324 of the shoulder-wear member 320 are connected with the ring connecti o n portions 346 of the back supporting member 340, in correspondence to each other. The combining bands 358 of the waist band member 350 are combined with the band combining portions 344 of the back supporting member 340. Accordingly, the back supporting member 340, the shoulder-wear member 320, and the waist band member 350 are connected in one body. Here, the waist band member 350 is located between the back supporting member 340 and the shoulder-wear member 320. The battery case 330 is inserted into the battery case holder 316 formed on the rear surface of the back supporting member 340. The ultrasonic diagnoser 310 is inserted into and loaded in the space of the back supporting member 340, The state of the completely assembled ultrasonic diagnostic apparatus 300 is shown in FIG. 5.

The ultrasonic diagnostic apparatus 300 according to the second embodiment of the present invention accommodates the ultrasonic diagnoser 310 in the accommodation space formed in the back supporting member 340 swiftly and conveniently, to thereby keep or carry it.

Figure 6:
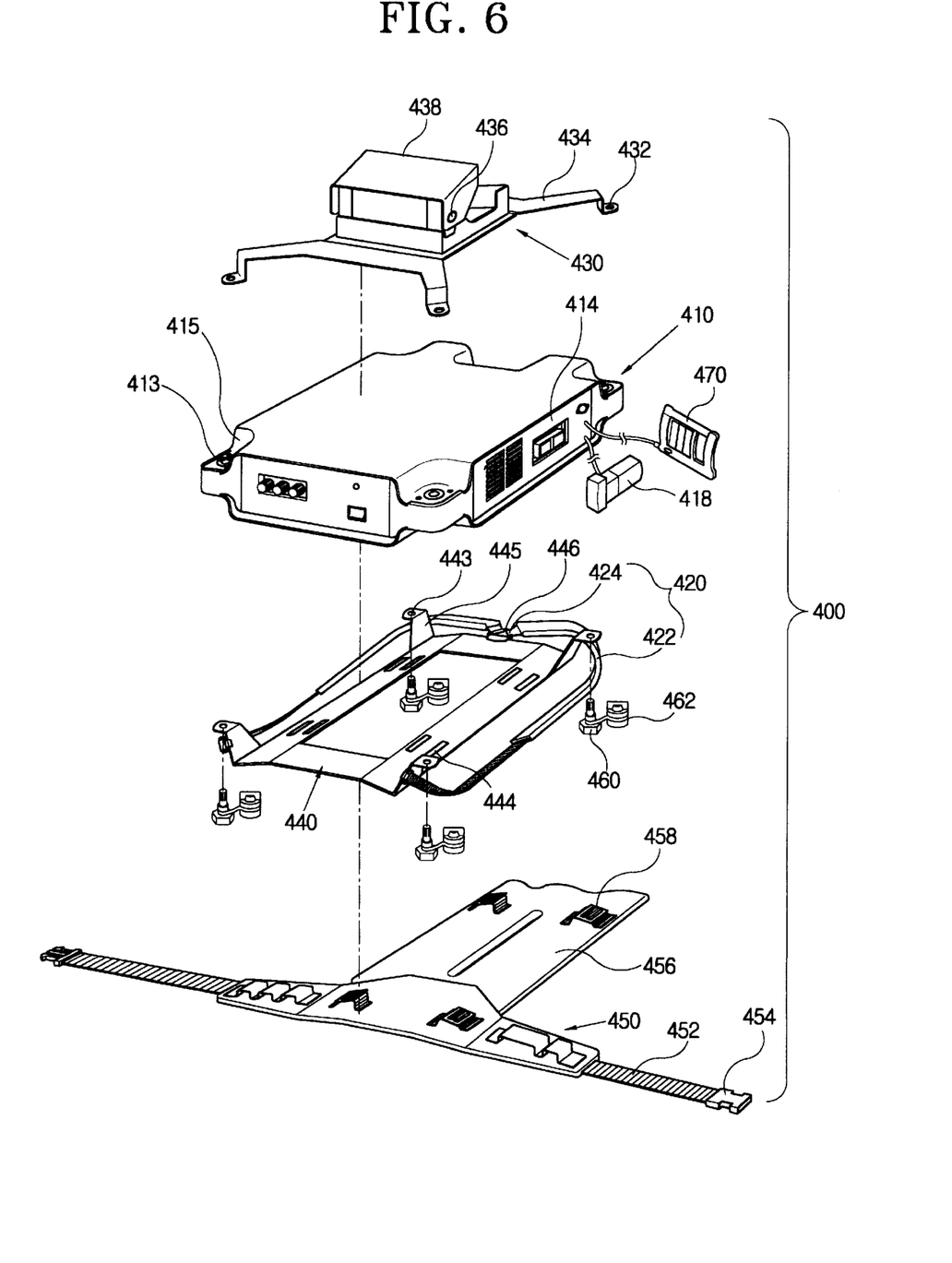
FIG. 6 is a perspective view of a disassembled state of a third preferred embodiment of the present invention.
Figure 7:
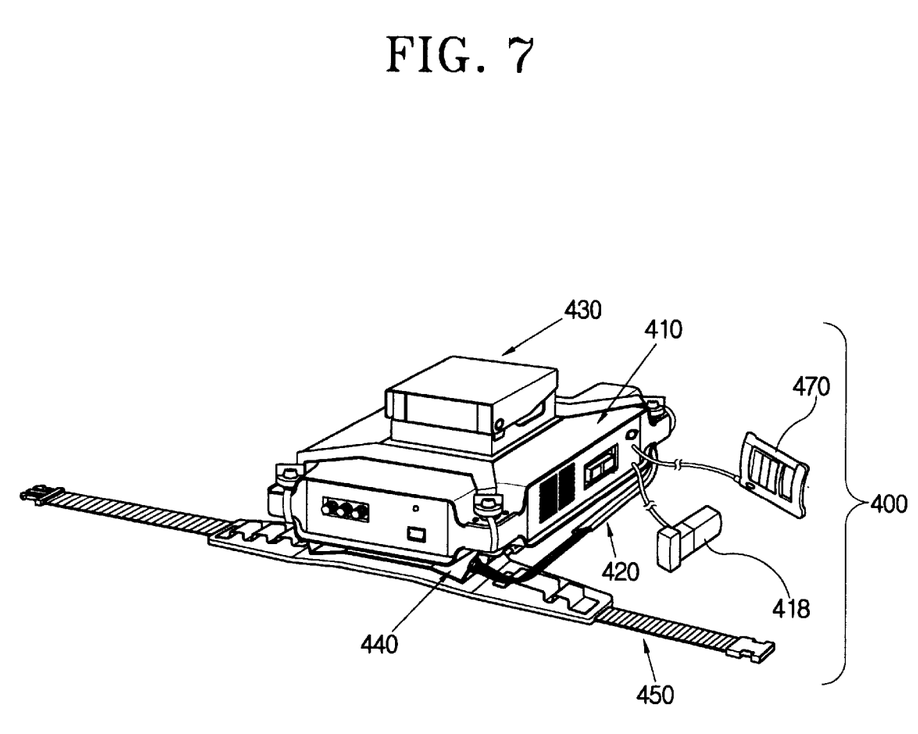
FIG. 7 is a perspective view of an assembled state of the third embodiment.

FIG. 6 is a perspective view of a disassembled state of a third preferred embodiment of the present invention. FIG. 7 is a perspective view of an assembled state of the third embodiment.

An ultrasonic diagnostic apparatus 400 of the third embodiment is shown in FIG. 6. The ultrasonic diagnostic apparatus 400 is comprised of an ultrasonic diagnoser 410 and a shoulder-wear member 420. The ultrasonic diagnostic apparatus 400 is also comprised of a battery case 430, a back supporting member 440 and a waist band member 450. The ultrasonic diagnostic apparatus 400 also includes an external monitor 470. A terminal plate 414 is formed in the lateral surface of the ultrasonic diagnoser 410, and a probe 418 and the external monitor 470 are connected on the terminal plate 414. In each corner of the ultrasonic diagnoser 410 are formed a throughhole 413 and a combining portion 415 whose both surfaces are concave by a predetermined depth. The shoulder-wear member 420 is comprised of a shoulder strap 422 and rings 424 formed on respective ends of the shoulder strap 422. The battery case 430 is formed as a substantially box-shaped hexahedron corresponding to the shape of the outer sheathed battery. One surface of the battery case 420 is open in part so that the outer sheathed battery can be inserted into or removed from it. An opening and shutting cover 438 is rotatably fixed with a hinge 436, on the partly open one surface of the battery case. Also, on each corner of the other one surface opposing the battery case 430 is formed a supporting leg 434 extended outwards by a predetermined length and bent in the form corresponding to the combining portion 415 of the ultrasonic diagnoser 410. On each corner of the back supporting member 440 is formed a supporting leg 445 which is same as that of the battery case 430. On the supporting legs 445 are formed throughholes 443 corresponding to the throughholes 413 of the ultrasonic diagnoser 410. Three ring connection portions 446 are formed in the upper and lower edges of the back supporting member 440, and four band combining portions 444 are formed therein. The waist band member 450 is comprised of a belt 452, a pair of buckles 454 mutually corresponding to either end of the belt 452. The waist band member 450 includes a buffer member 456 corresponding to the back supporting member 440. Also, one surface of the waist band member 450 are formed four combining bands 458.

The battery case 430 is closely attached to the rear surface of the ultrasonic diagnoser 410 and the back supporting member 440 is closely attached to the front surface thereof. The supporting legs 434 and 445 of the battery case 430 and the back supporting member 440 are safely loaded into the combining portion 415 of the ultrasonic diagnoser 410. Bolts 460 are inserted into throughholes 413, 432 and 443 of the ultrasonic diagnoser 410, the battery case 430 and the back supporting member 440 all of which are closely attached, and then bolts 460 are tightened by nuts 462. Rings 424 of the shoulder-wear member 420 are connected with the ring connection portions 446 of the back supporting member 440. The combining bands 458 of the waist band member 450 are combined with the band combining portions 444 of the back supporting member 440. Accordingly, the members such as ultrasonic diagnoser 410, the shoulder-wear member 420, and so on are connected in one body. The state of the completely assembled ultrasonic diagnostic apparatus 400 is shown in FIG. 7.

The ultrasonic diagnostic apparatus 400 according to the third embodiment of the present invention can maintain a firm combination by bolt-tightening the ultrasonic diagnoser 410 and the members 420 and 430. Thus, even one of the members including the ultrasonic diagnoser 410 in use can be hardly detached from the ultrasonic diagnostic apparatus 400, thereby improving a stability in use of the ultrasonic diagnostic apparatus 400.

As described above, the ultrasonic diagnostic apparatus according to the present invention is comprised of a shoulder-wear member so that a user can wear or carry the ultrasonic diagnoser on the shoulder. As a result, an activity for diagnosing a health condition of animals can be done more efficiently.

Also, the ultrasonic diagnostic apparatus according to the present invention which can be used with the ultrasonic diagnoser accommodated in an accommodation space of the back supporting member, connects the shoulder-wear member and the ultrasonic diagnoser swiftly and conveniently to portably use or carry it.

Also, the ultrasonic diagnostic apparatus according to the present invention in which the ultrasonic diagnoser and the relevant members are bolt-tightened so that a firmer combination can be maintained, provides an effect of improving a safety in use.

What is claimed is:

1. A portable ultrasonic diagnostic apparatus having a probe for veterinary activity, the portable ultrasonic diagnostic apparatus comprising:
   an ultrasonic diagnosing member for transmitting and receiving ultrasonic signals through the probe and processing signals received from the probe; and
   a shoulder-wear member releasably attached to the ultrasonic diagnosing member to enable the ultrasonic diagnosing member to be worn on the shoulder, the shoulder-wear member including a back supporting member for facilitating resting of the ultrasonic diagnosing member on the back of a human body.

2. The portable ultrasonic diagnostic apparatus of claim 1, wherein said ultrasonic diagnosing member comprises a battery case which is removably mounted to a surface of the ultrasonic diagnosing member opposite the back supporting member.

3. The portable ultrasonic diagnostic apparatus of claim 1, wherein the back supporting member includes a buffer member for absorbing mechanical impact upon the back.

4. The portable ultrasonic diagnostic apparatus of claim 3, wherein the back supporting member further includes a belt for supporting the ultrasonic diagnosing member to the human body.

5. The portable ultrasonic diagnostic apparatus of claim 1, further comprising an external monitor connected to the ultrasonic diagnosing member in order to output a detected signal as an ultrasonic image.

6. A portable ultrasonic diagnostic apparatus having a probe for veterinary activity, the portable ultrasonic diagnostic apparatus comprising:

an ultrasonic diagnosing member;

a box-shaped back supporting member having a space accommodating the ultrasonic diagnosing member; and a shoulder-wear member which is connected to the back supporting member in order to enable the ultrasonic diagnosing member to be worn on the shoulder.

7. A portable ultrasonic diagnostic apparatus of claim 6, further comprising a battery case which is assembled or disassembled to one surface of the back supporting member, in order to accommodate at least one outer sheathed battery.

8. A portable ultrasonic diagnostic apparatus of claim 6, further comprising a waist band member connected to the back supporting member in which a belt and a mutually corresponding pair of buckles in each end of the belt are formed.

9. A waist band member of claim 8, further comprising a buffer member for protecting a human body from a mechanical shock transmitted from the ultrasonic diagnosing member.

10. A portable ultrasonic diagnostic apparatus of claim 6, further comprising an external monitor connected to the ultrasonic diagnosing member in order to output a detected signal as an ultrasonic image.

11. A portable ultrasonic diagnostic apparatus having a probe for veterinary activity, the portable ultrasonic diagnostic apparatus comprising:

an ultrasonic diagnosing member having an engagement portion pierced with a throughhole and formed in each corner portion;

a battery case including an opening and shutting cover hinge-combined and a supporting leg pierced with a throughhole corresponding to the engagement portion of the ultrasonic diagnosing member in each corner portion, and being combined with one surface of the ultrasonic diagnosing member;

a back supporting member having a supporting leg pierced with a throughhole corresponding to the engagement portion of the ultrasonic diagnosing member in each corner portion and combined with the other surface of the ultrasonic diagnosing member; and a shoulder-wear member which is connected to the back supporting member in order to enable the ultrasonic diagnosing member to be worn on the shoulder.

12. A portable ultrasonic diagnostic apparatus of claim 11, wherein both surfaces of the engagement portion of the ultrasonic diagnosing member are concave by a predetermined depth, and the supporting legs of the back supporting member and the battery case are bent in correspondence to the engagement portion.

13. A portable ultrasonic diagnostic apparatus of claim 11, further comprising a waist band member connected to the back supporting member in which a belt and a mutually corresponding of buckle in each end of the belt is formed.

14. A waist band member of claim 13, further comprising a buffer member for protecting a human body from a mechanical shock transmitted from the ultrasonic diagnosing member.

15. A portable ultrasonic diagnostic apparatus of claim 11, further comprising an external monitor connected to the ultrasonic diagnosing member in order to output a detected signal as an ultrasonic image.

\* \* \* \* \*